United States Patent [19]

Levitt

[11] 4,302,241

[45] Nov. 24, 1981

[54] AGRICULTURAL SULFONAMIDES

[75] Inventor: George Levitt, Wilmington, Del.

[73] Assignee: E. I. Du Pont de Nemours and Company, Wilmington, Del.

[21] Appl. No.: 98,779

[22] Filed: Nov. 30, 1979

Related U.S. Application Data

[63] Continuation-in-part of Ser. No. 53,977, Jul. 2, 1979, abandoned.

[51] Int. Cl.³ ............... A01N 43/54; C07D 413/00; C07D 239/02; C07D 403/00
[52] U.S. Cl. ........................................... 71/92; 71/93; 544/113; 544/114; 544/211; 544/312; 544/321; 544/332
[58] Field of Search ............ 71/92, 103, 120, 107; 544/297, 321, 312, 332

[56] References Cited

U.S. PATENT DOCUMENTS

| | | | |
|---|---|---|---|
| 3,497,344 | 2/1970 | Le Fevre et al. | 71/92 |
| 3,736,122 | 5/1973 | Tung et al. | 71/92 |
| 3,867,452 | 2/1975 | Wilcox | 71/107 |
| 4,111,683 | 9/1978 | Singer | 71/92 |
| 4,191,553 | 3/1980 | Reap | 71/92 |

*Primary Examiner*—Glennon H. Hollrah

[57] ABSTRACT

This invention relates to novel N-(heterocyclicaminocarbonyl)arylsulfonamides in which the aryl radical is substituted by two carboxyl radicals. The compounds have utility as herbicides.

19 Claims, No Drawings

AGRICULTURAL SULFONAMIDES

CROSS-REFERENCE TO RELATED APPLICATION

This application is a continuation-in-part of my copending application U.S. Ser. No. 053,977 filed July 2, 1979, now abandoned.

BACKGROUND OF THE INVENTION

This invention relates to novel N-(heterocyclicaminocarbonyl)arylsulfonamides in which the aryl radical is substituted by two carboxyl radicals. The compounds of this invention and their agriculturally suitable salts, are useful as agricultural chemicals, e.g. plant growth regulants and herbicides.

Netherlands Patent No. 121,788, published Sept. 15, 1966, discloses the preparation of compounds of the following Formula and their use as general or selective herbicides:

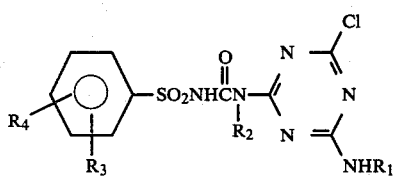

wherein
  $R_1$ and $R_2$ may independently be alkyl of 1–4 carbon atoms; and
  $R_3$ and $R_4$ may independently be hydrogen, chlorine or alkyl or 1–4 carbon atoms.

U.S. Pat. No. 3,637,366 discloses compounds having the formula:

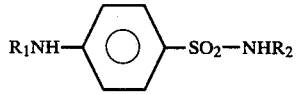

wherein
  $R_1$ is hydrogen or lower saturated aliphatic acyl and
  $R_2$ is hydrogen, 2-pyrimidinyl, pyridyl, amidino, acetyl or carbamoyl.

The disclosed compounds are said to provide control of crabgrass, cress, endive, clover and *Poa annua*.

French Patent. No. 1,468,747 discloses the following para-substituted phenylsulfonamides as being useful as antidiabetic agents:

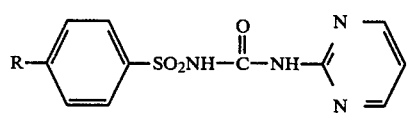

wherein R=H, halogen, $CF_3$ or alkyl:

Logemann et al. Chem. Ab., 53 18052 g (1959), disclose a number of sulfonamides, including uracil derivatives and those having the formula:

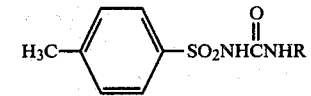

wherein
  R is butyl, phenyl, or

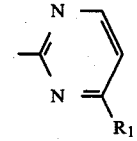

and
  $R_1$ is hydrogen or methyl.
When tested for hydroglycemic effect in rats (oral doses of 25 mg/100 g), the compounds in which R is butyl and phenyl were most potent. The others were of low potency or inactive.

Wojciechowski, J. Acta. Polon. Pharm 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

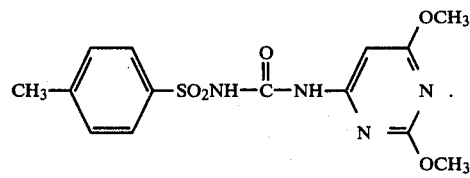

Based upon similarity to a known compound, the author speculated that the foregoing compound might have a hypoglycemic activity.

Substituted-pyrimidinyl sulfonylureas of the following formula, which are also para-substituted on the phenyl ring, are disclosed in Farmco Ed. Sci., 12, 586 (1957) [Chem. Ab., 53, 18052 g (1959)];

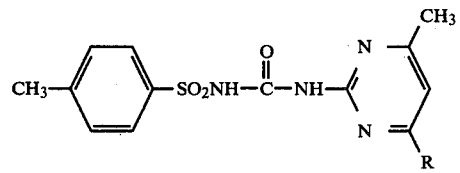

wherein R=H or $CH_3$.

The presence of undesired vegetation causes substantial damage to useful crops, especially agricultural products that satisfy man's basid food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency. A wide variety of materials useful for killing or inhibiting (controlling) the growth of undesired vegetation is available; such materials are commonly referred to as herbicides. The need still exists however, for more effective herbicides.

SUMMARY OF THE INVENTION

According to this invention, there are provided novel compounds of Formula I and their agriculturally suitable salts, e.g., Na, K, alkyl ammonium, trichloroacetic acid, suitable agricultural compositions containing them and methods of using these compounds as agricultural chemicals

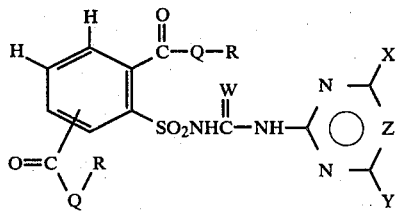

wherein
Q is O or

W is O or S;
when Q is O, then R is $C_1$–$C_4$ alkyl, $C_3$–$C_4$ alkenyl, $CH_2CH_2Cl$ or $CH_2CH_2OCH_3$;
when Q is

then R is H, $C_1$–$C_4$ alkyl or $C_3$–$C_4$ alkenyl;
$R_1$ is H, $C_1$–$C_4$ alkyl, and R and $R_1$ can be taken together to form —$(CH_2)_4$—, —$(CH_2)_5$—, and —$CH_2CH_2O$—$CH_2CH_2$—;
X is $CH_3$, $CH_3O$, $CH_3CH_2O$ or Cl;
Y is $CH_3$, $CH_3O(CH_2)_{n'}$ where n' is 0, 1 or 2, $CH_3CH_2O$, or $R^2O_2CCHR^1O$ where $R^1$ is H or $CH_3$ and $R^2$ is H or $C_1$–$C_3$ alkyl;
Z is CH, N, or C—$CH_3$;
with the proviso that when Q is

then the floating

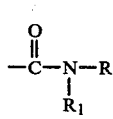

must be in the 3 position.
Preferred compounds for their higher activity and/or ease of synthesis are:
(1) those compounds of the generic scope in which W is O;
(2) those compounds of Preferred 1 in which Q is oxygen;
(3) those compounds of Preferred 2 in which Y is $CH_3$—, —$OCH_3$ or

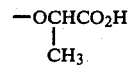

and X is $CH_3$, $CH_3O$ or $CH_3CH_2O$;
(4) those compounds of Preferred 3 in which R is $CH_3$ or —$CH_2CH_3$.

Specifically preferred for their extremely high biological activity or their very highly favorable ease or synthesis, or both, are the following compounds:
2-{[(4,6-dimethoxypyrimidin-2-yl)aminocarbonyl]-aminosulfonyl}-1,4-benzenedicarboxylic acid, dimethyl ester;
2-{[(4,6-dimethoxy-1,3,5-triazin-2-yl)aminocarbonyl]aminosulfonyl}-1,4-benzenedicarboxylic acid, dimethyl ester;
2-{[(4-methoxy-6-methylpyrimidin-2-yl)aminocarbonyl]aminosulfonyl}-1,4-benzenedicarboxylic acid, dimethyl ester;
2-{[(4,6-dimethylpyrimidin-2-yl)aminocarbonyl]-aminosulfonyl}-1,4-benzenedicarboxylic acid, dimethyl ester;
2-{[(4,6-dimethyl-1,3,5-triazin-2-yl)aminocarbonyl]-aminosulfonyl}-1,4-benzenedicarboxylic acid, dimethyl ester;
2-{[(4-methoxy-6-methyl-1,3,5-triazin-2-yl)aminocarbonyl]aminosulfonyl}-1,4-benzenedicarboxylic acid, dimethyl ester;
2-{([4-(2-ethoxy-1-methyl-2-oxoethoxy)-6-methyl-1,3,5-triazin-2-yl]aminocarbonyl)aminosulfonyl}-1,4-benzenedicarboxylic acid, dimethyl ester;
2-{[(4,6-dimethoxypyrimidin-2-yl)aminocarbonyl]-aminosulfonyl}-1,4-benzenedicarboxylic acid, dipropyl ester;
2-{[(4,6-dimethoxy-1,3,5-triazin-2-yl)aminocarbonyl]aminosulfonyl}-1,4-benzenedicarboxylic acid, dipropyl ester;
2-{[(4-methoxy-6-methyl-1,3,5-traizin-2-yl)aminocarbonyl]aminosulfonyl}-1,4-benzenedicarboxylic acid, dipropyl ester;
2-[[(4,6-dimethoxy-1,3,5-triazin-2-yl)aminocarbonyl]aminosulfonyl]-1,3-benzenedicarboxylate, dimethyl ester.

DETAILED DESCRIPTION OF THE INVENTION

Synthesis

The compounds of Formula I can be prepared as shown in Equations 1 through 4.

Equation 1

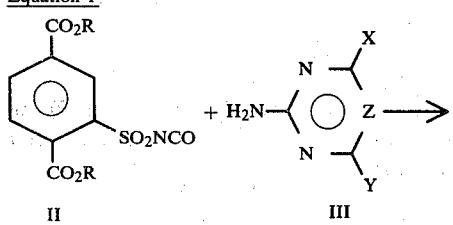

-continued

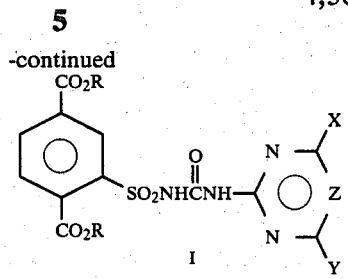

(R, X, Y and Z are as defined above)

Thus 2-(isocyanatosulfonyl)-1,4-benzenedicarboxylates II are important intermediates in preparing the instant compounds. These intermediates are in turn prepared from the corresponding 2-(aminosulfonyl)-1,4-benzenedicarboxylates and phosgene as shown in Equation 2. Using this procedure, compounds of Formula I where the floating carboxylate is in the 4-position can be prepared.

Equation 2

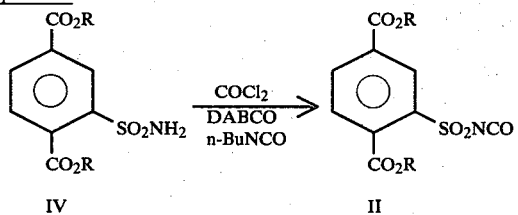

The 2-(aminosulfonyl)-1,4-benzenedicarboxylates are converted to the corresponding isocyanate, (Eq. 2) by heating from 120° to 135° C. a mixture of the sulfonamide, an alkyl isocyanate, such as butyl isocyanate, and a catalytic amount of 1,4-diaza[2.2.2]bicyclooctane in xylene, or other inert solvent of sufficiently high boiling point (e.g. 135°), such as o-dichlorobenzene.

Phosgene is added until an excess is present as indicated by a drop in the boiling point. The mixture is heated to about 135° C. to drive off excess phosgene then cooled to about 25° C. and filtered to remove any insoluble by-products. The solvent and alkyl isocyanate are distilled in-vacuo giving a residue of crude sulfonyl isocyanate (II). This material can be used directly or purified by appropriate techniques.

As shown in Equation 1, compounds of Formula I are conveniently prepared from compounds of Formula II and the appropriately substituted aminopyrimidine or aminotriazine (III).

The reaction of Equation 1 is best carried out in inert aprotic solvents such as methylene chloride, tetrahydrofuran or acetonitrile, at ambient pressure and temperature. The mode of addition is not critical; however, it is often convenient to add the sulfonyl isocyanate to a stirred suspension of amine III. Since such isocyanates are liquids, low melting solids or, are readily soluble in solvents such as those listed above, their addition can be easily controlled.

The reaction is generally exothermic. In some cases, the desired product is soluble in the warm reaction medium and on cooling crystallizes in pure form. Other products which are soluble in the reaction medium are isolated by evaporation of the solvent, trituration of the solid residue with solvents such as 1-chlorobutane or ethyl ether, and filtration.

The synthesis of heterocyclic amines has been reviewed in "The Chemistry of Heterocyclic Compounds" a series published by Interscience Publ., New York and London. 2-Aminopyrimidines are described by D. J. Brown in "The Pyrimidines", Vol. XVI of this series. The 2-amino-1,3,5-triazines are reviewed by K. R. Huffman and in "The Triazines" of this same series. The synthesis of triazines are also described by F. C. Schaefer, U.S. Pat. No. 3,154,547 and by K. R. Huffman and F. C. Schaefer, J. Org. Chem. 28, 1816–1821 (1963).

Equation 3

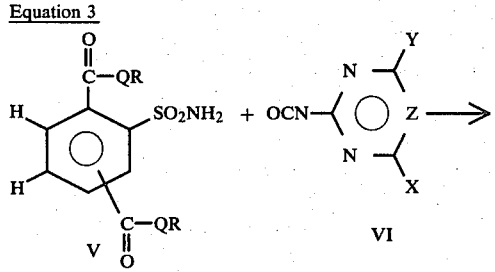

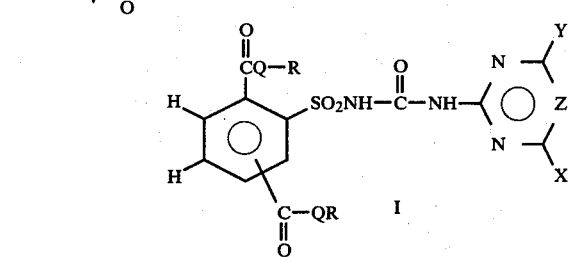

Compounds of Formula I in which X is $OCH_3$ or $OCH_2CH_3$ can also be prepared as shown in Equation 3A.

Equation 3A

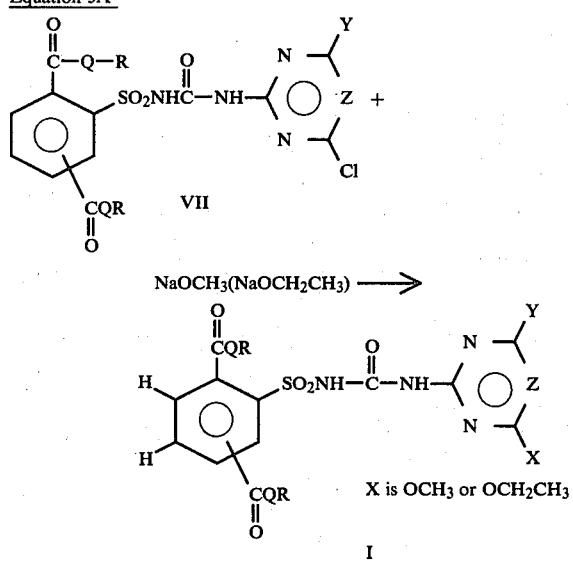

The heterocyclic isocyanate VI is prepared as described in Angew, Chem. Int. Ed. Engl. 10, 402 (1971). To one equivalent of the appropriately substituted benzenesulfonamide (V) in an inert aprotic solvent such as methylene chloride, tetrahydrofuran or acetonitrile is added one or more equivalents of isocyanate VI followed by refluxing 1 to 24 hours. The product may be isolated by evaporation of the solvent, trituration of the solid residue with solvents such as 1-chlorobutane or ethyl ether, and filtration.

To one equivalent of compound VII in alcoholic solvent is added 3 equivalents of the corresponding sodium alkoxide. The mixture is stirred for about 0.5 hours followed by the addition of water and acidification with dilute hydrochloric acid.

Compounds of Formula I in which W is S are prepared as shown in Equation 4.

Equation 4

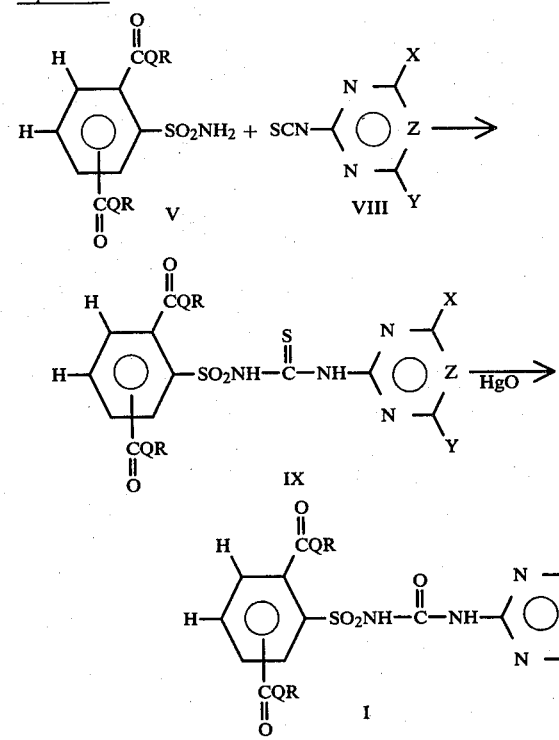

The heterocyclic isothiocyanate (VIII) can be prepared according to the methods of Japanese Patent: Kokai No. 51-143686, June 5, 1976, or of W. Abraham and G. Barnikow, Tetrahedron 29, 691-7 (1973).

The reaction of Equation 4 is best carried out by dissolving or suspending the sulfonamide and isothiocyanate in a polar solvent such as acetone, acetonitrile, ethyl acetate or methylethylketone, adding an equivalent of a base such as potassium carbonate and stirring the mixture at ambient temperature up to the reflux temperature for 1 to 24 hours.

Compounds of Formula IX can be isolated by evaporation of the solvent and trituration of the residue with dilute mineral acid and filtering off the insoluble product.

Compounds of Formula I can be prepared by the addition of one equivalent of mercuric oxide to a solution of compound IX in acetone, acetonitrile or tetrahydrofuran and stirred for 1 to 24 hours followed by filtration of mercuric sulfide and evaporation of the solvent.

The 2-(aminosulfonyl)-1,4-benzenedicarboxylates above can be prepared according to Scheme 1. This route was described in *J. of Pharm. and Pharmacology* 14, 679 (1962), the disclosure of which is herein incorporated by reference.

Scheme 1

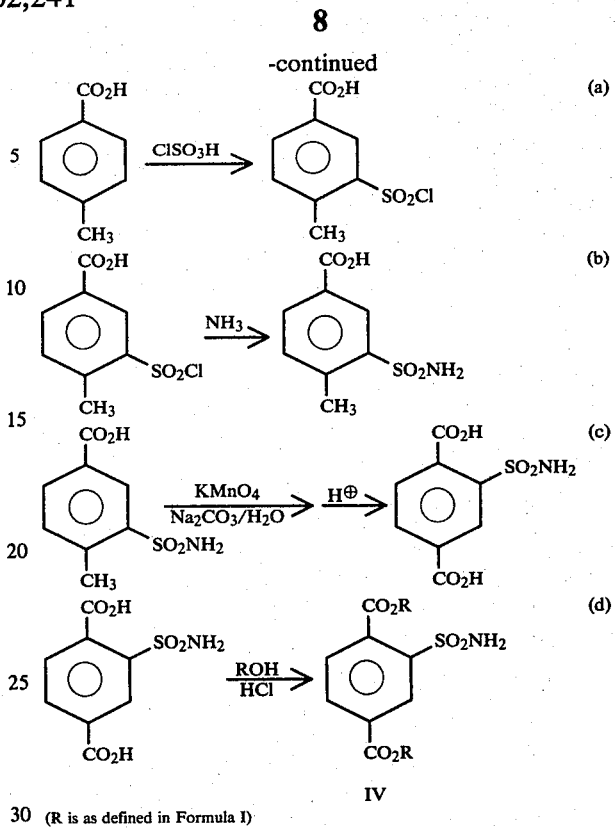

(R is as defined in Formula I)

Compounds of Formula IV where R is other than $CH_2CH\!=\!CH_2$ can be prepared according to Scheme 2.

Scheme 2

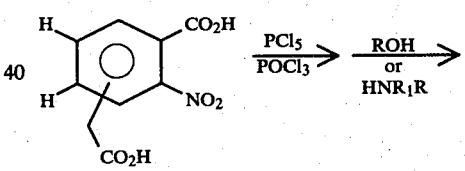

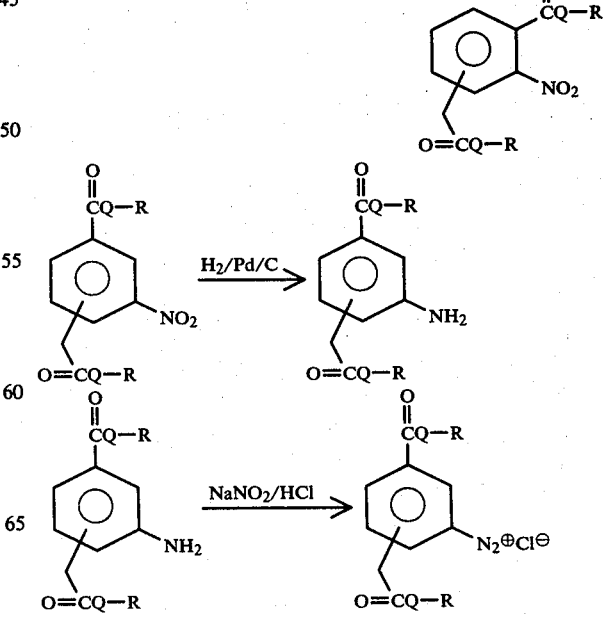

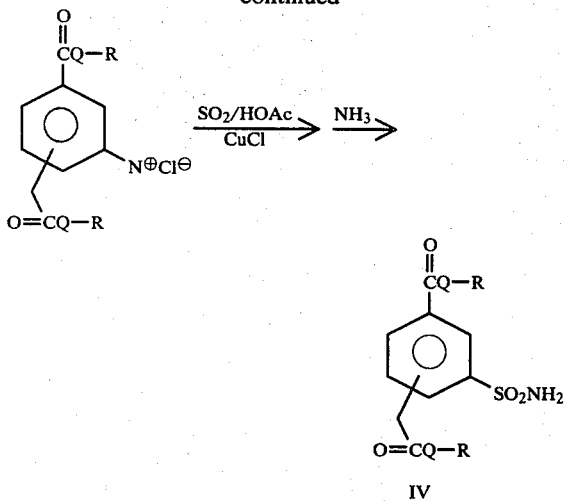

Compounds of Formula IV where Q is oxygen and R is CH$_2$CH=CH$_2$ and other alkyls can also be prepared according to Scheme 3.

Scheme 3

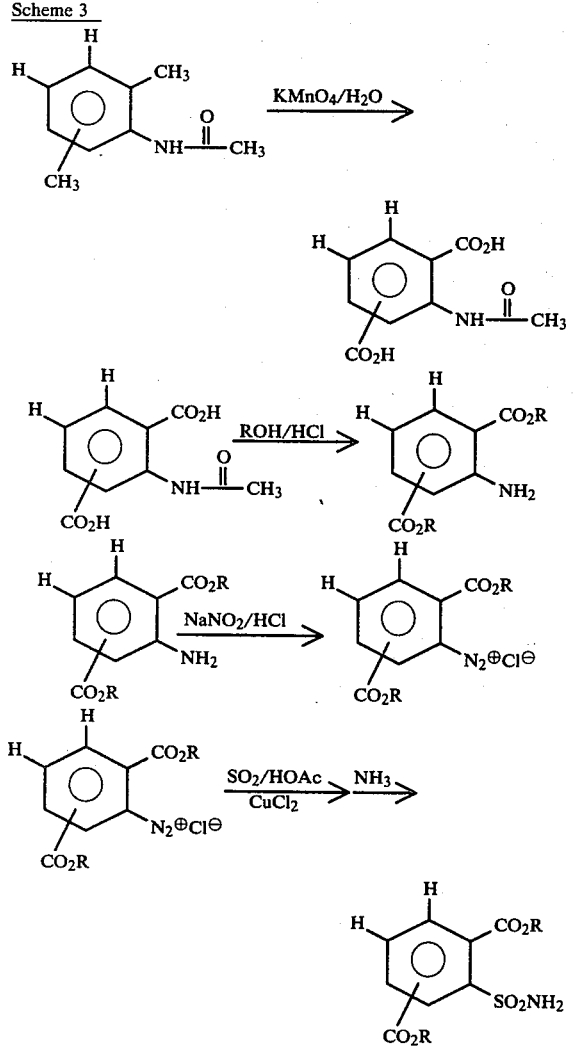

The preparation of agriculturally suitable salts of the compounds of Formula I, as well as starting materials and intermediates for said compounds, not otherwise described herein, is disclosed in U.S. Pat. No. 4,217,405, the contents of which are incorporated herein by reference.

The compounds of this invention and their preparation are further illustrated by the following examples wherein temperatures are given in degrees centigrade and parts by weight unless otherwise indicated.

EXAMPLE 1

3-(Aminosulfonyl)-4-methylbenzoic Acid

To a stirred solution of 200 ml of chlorosulfonic acid cooled to 5°–15° was added 68 g of p-toluic acid. The mixture was heated for 6 hours at 120°–130° and then poured onto ice. The mixture was then extracted with chloroform. The extract was washed with ice water, dried over magnesium sulfate, filtered and stripped to yield 43 g of sulfonyl chloride (m.p. 168°–170°) product. The product was then added, in portions, to 400 ml of liquid ammonia with rapid stirring and then allowed to evaporate at room temperature to dryness, overnight. The resulting residue was dissolved in H$_2$O acidified, filtered, washed with H$_2$O and dried to give 36.9 g of solid; m.p. 275°–277°, 3-(aminosulfonyl)-4-methyl benzoic acid.

EXAMPLE 2

2-(Aminosulfonyl)-1,4-benzenedicarboxylic Acid

To a solution of 44 g of 3-(aminosulfonyl)-4-methyl benzoic acid (Example 1) in 500 ml H$_2$O was added 11.0 g of sodium carbonate and 72 g of potassium permanganate in 8 g portions at 50°–60° over 5.5 hours. Then, 1 ml formic acid was added to decompose excess oxidant and the solution was filtered hot (60°) through Celite. The filter pad was washed with hot water. The combined filtrate was concentrated, in vacuo to approximately 300 ml and brought to pH 6 with concentrated HCl. A small amount of solid was filtered off. The filtrate was brought to pH 3.5 with concentrated HCl. The resulting solid was collected, washed with water and dried to give 33 g of solid; m.p. 259-290 (known m.p. 312-314). This material was used, without further purification, in Example 3.

EXAMPLE 3

Dimethyl 2-(Aminosulfonyl)-1,4-benzenedicarboxylate

To the product isolated in Example 2 was added 300 ml methanol. The mixture was refluxed for 4 hours while HCl was bubbled in, then refluxed, overnight. The solution was filtered (hot), and the filtrate stripped. The residue was recrystallized from isopropanol to give 14 g of product; m.p. 120°–130°. This product was recrystallized three times from 1-chlorobutane and a small amount of acetonitrile to give 2.9 g of dimethyl 2-(aminosulfonyl)-1,4-benzenedicarboxylate; m.p. 165°–170°. A melting point for the same product was found to be 171°–173° in the *J. of Pharm. and Pharmacology* 14, 679 (1962).

EXAMPLE 4

Dimethyl 2-Nitro-1,4-benzenedicarboxylate

To 150 ml of phosphorous oxychloride was added, with stirring, 211 g of 2-nitro-1,4-benzenedicarboxylic acid. To this mixture was added 425 g of phosphorous pentachloride in portions so that foaming was controlled. The mixture was heated to reflux (108°) until gas evolution ceased, then the phosphorous oxychloride was removed in-vacuo to give 268 g of residue. The residue was added over 0.75 hours to 200 ml of methanol. The solution temperature was allowed to rise to reflux during the addition and refluxing was continued for 1.75 hours longer. The mixture was then stripped and the residue recrystallized from acetonitrile and 1-chlorobutane (1:6) to give 137 g off white solid; m.p. 72.5°–74°, dimethyl 2-nitro-1,4-benzenedicarboxylate.

EXAMPLE 5

Dimethyl 2-Amino-1,4-benzenedicarboxylate

A Parr Shaker was charged with 50 g of dimethyl 2-amino-1,4-benzenedicarboxylate, 250 ml methanol, and 2.0 g of 5% palladium on charcoal. The Shaker bottle was then charged with hydrogen at 50 p.s.i. and shaken until hydrogen uptake had ceased (approximately 1 hour). The reaction mixture was filtered and the filter cake washed with DMF. The combined filtrates were stripped to dryness and the residue washed with methanol, filtered and dried to give 35.3 g solid; m.p. 132°–134°, dimethyl 2-amino-1,4-benzenedicarboxylate.

EXAMPLE 6

Dimethyl 2-(Aminosulfonyl)-1,4-benzedicarboxylic Acid from Dimethyl 2-Amino-1,4-benzenedicarboxylate To a mixture of 112.8 g of dimethyl 2-amino-1,4-benzenedicarboxylate, in 400 ml concentrated HCl and 120 ml acetic acid, at 0°–3° was added, dropwise, a solution of 51.8 g sodium nitrite in 140 ml water over 0.75 hours. The mixture was then stirred at 0° for 10 minutes and poured into a mixture of 575 ml acetic acid, 14 g cuprous chloride and 100 ml sulfur dioxide at 0°–5° over 10 minutes. The mixture was stirred at 0°–5° for 0.25 hours then warmed to room temperature and stirred for 3 hours. It was poured into 3 liters of ice water and extracted with diethyl ether. The ether was washed three times with water, then with saturated sodium bicarbonate until basic and then washed with water once again. The solution was dried over magnesium sulfate and filtered to give ~800 ml of solution. The solution was cooled to 10°–20° and 20 ml of liquid ammonia added dropwise. It was stirred for 0.5 hours at 25°. The solid that formed was collected, washed with diethyl ether, then washed four times with water and finally washed with methanol (50 ml). The product was dried to give 98.5 g; m.p. 167°–170° of dimethyl 2-(aminosulfonyl)-1,4-benzenedicarboxylic acid.

EXAMPLE 7

Dimethyl 2-(Isocyanatosulfonyl)-1,4-benzenedicarboxylate

A stirred mixture of 95.6 g of dimethyl 2-(aminosulfonyl)-1,4-benzenedicarboxylic acid, 35.5 g of n-butylisocyanate, 0.5 g of 1,4-diazabicyclo[2.2.2]octane and 400 ml of xylene was heated to reflux for one half hour. Phosgene gas was then passed into the system under a dry ice reflux condenser allowing the reaction temperature to drop to 120°. This addition was continued until the reflux temperature remained at 120° without further phosgene addition (2.75 hours). The temperature of the reaction mixture was then raised to 136° (by removal of the dry ice reflux condenser) after which it was cooled to room temperature and filtered. Evaporation of the filtrate yielded the desired crude sulfonyl isocyanate, which was used for subsequent reactions without purification. The product is extremely reactive with water so contact with moisture should be avoided.

The compound was identified by conversion to the next product.

Using the procedure exemplified above, the compounds of Table III can be prepared.

EXAMPLE 8

Dimethyl 2-[[(4,6-Dimethylpyrimidin-2-yl)aminocarbonyl]-aminosulfonyl]-1,4-benzenedicarboxylate To 32 g of 2-amino-4,6-dimethylpyrimidine in 300 ml of acetonitrile was added a trace of 1,4-diazabicyclo[2.2.2]octane followed by slow addition over 15–20 minutes of 97 g of dimethyl 2-(isocyanatosulfonyl)-1,4o-benzenedicarboxylate in 90 ml of acetonitrile. The temperature rose to 36° and the reaction was stirred at room temperature overnight. The mixture was filtered and the solid washed twice with acetonitrile, once with 1-chlorobutane and dried to give 81.8 g of solid; m.p. 177°–180°, dimethyl 2-[[(4,6-dimethylpyrimidin-2-yl)aminocarbonyl]aminosulfonyl]-1,4-benzenedicarboxylate.

EXAMPLE 9

Dimethyl 2-[[4-Methoxy-6-methyl-1,3,5-triazin-2-yl)aminocarbonyl]aminosulfonyl]-1,4-benzenedicarboxylate To 1.3 g of 2-amino-4-methoxy-6-methyltriazine in 20 ml acetonitrile containing a trace of 1,4-diazabicyclo[2.2.2.]octane was added by slow addition, 3.75 g of dimethyl-2-(isocyanatosulfonyl)-1,4-benzenedicarboxylate in 3.4 ml acetonitrile. The mixture was stirred overnight at room temperature, filtered and the resulting solid washed with acetonitrile and dried to give 3.1 g white solid; m.p. 173°–175°, dimethyl 2-[[4-methoxy-6-methyl-1,3,5-triazin-2-yl)aminocarbonyl]-aminosulfonyl]-1,4-benzenedicarboxylate.

Using the procedures exemplified, the compounds of Tables I and II can be prepared. These tables are not all inclusive but only illustrative of the scope of this application.

EXAMPLE 10

Dimethyl 2-(chlorosulfonyl)-1,3-benzenedicarboxy] and from 2-amino-1,3-benzenedicarboxylate To a mixture of 20 g dimethyl 2-amino-1,3-benzenedicarboxylate prepared by the procedures of Scheme 3 (Hirsch et al., J. Org. Chem. 39, p. 2044-8 (1974) in 150 ml concentrated HCl at 0°–5° was added, dropwise, a solution of 7.2 g sodium nitrite in 10 ml water over 10 minutes.

The mixture was stirred at 0° for 0.5 hours and poured into a mixture of 150 ml acetic acid, 6 g cupric chloride in 6 ml water, and 40 ml sulfur dioxide over 10 minutes and stirred for 2 hours.

After adding 100 ml diethyl ether, the solution was stirred 17 hours at room temperature. About 600 ml water was added to this solution and the solid which formed was collected, dissolve in methylene chloride, and dried with magnesium sulfate. Evaporation of the methylene chloride yielded 18.8 g, m.p. 110°–112°, of dimethyl 2-(chlorosulfonyl)-1,3-benzenedicarboxylic acid.

EXAMPLE 11

Dimethyl 2-(aminosulfonyl)-1,3-benzenedicarboxylic acid from dimethyl 2-(chlorosulfonyl)-1,3-benzenedicarboxylic acid To a mixture of 5 g dimethyl 2-(chlorosulfonyl)-1,3-benzenedicarboxylic acid and 1.4 g sodium bicarbonate in 25 ml tetrahydrofuran (dried over alumina) at 0°–5° was added, dropwise, a solution of 0.4 ml ammonia in 5 ml dry tetrahydrofuran. After stirring for 2 hours, the solution was evaporated, the resulting solid was washed with methylene chloride, then with water to give 2.4 g, m.p. 169° of dimethyl 2-(aminosulfonyl)-1,3-benzenedicarboxylic acid.

Using the methods described herein, the compounds of Tables I through VII can be prepared. These tables are not all inclusive but only illustrative of the scope of this application.

TABLE II

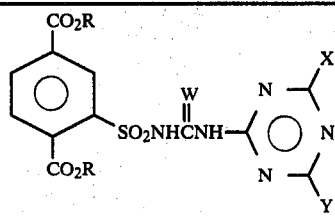

| R | X | Y | W | m.p. |
|---|---|---|---|---|
| —CH$_3$ | —OCH$_3$ | —OCH$_2$CH$_3$ | O | |
| —CH$_2$CH$_3$ | —OCH$_3$ | —OCH$_3$ | O | |
| —CH$_2$CH$_2$CH$_3$ | —OCH$_3$ | —OCH$_3$ | O | glass |
| —CH(CH$_3$)$_2$ | —OCH$_3$ | —OCH$_3$ | O | |
| —CH$_2$CH=CH$_2$ | —OCH$_3$ | —OCH$_2$CH$_3$ | O | |
| —CH$_2$CH$_2$Cl | —OCH$_3$ | —OCH$_3$ | O | |
| —CH$_3$ | —OCH$_3$ | —CH$_3$ | O | 173–175° |
| —CH$_2$CH$_3$ | —OCH$_3$ | —OCHCOCH$_2$CH$_2$CH$_3$ with CH$_3$ branch (—OCH(CH$_3$)COCH$_2$CH$_2$CH$_3$) | O | |
| —CH$_2$CH$_2$CH$_3$ | —OCH$_3$ | —CH$_2$OCH$_3$ | S | |
| —CH(CH$_3$)$_2$ | —OCH$_3$ | —CH$_2$CH$_2$OCH$_3$ | O | |
| —CH$_2$CH=CH$_2$ | Cl | —CH$_3$ | O | |

TABLE I

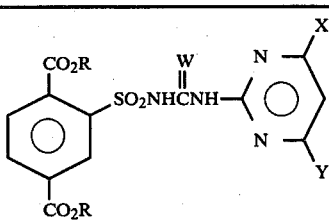

| R | X | Y | W | m.p. |
|---|---|---|---|---|
| —CH$_3$ | —CH$_3$ | —OCH$_3$ | O | 167–169° |
| —CH$_2$CH$_3$ | —CH$_3$ | —OCH$_3$ | O | |
| —CH$_2$CH$_2$CH$_3$ | —CH$_3$ | —OCH$_3$ | O | glass |
| —CH(CH$_3$)$_2$ | —CH$_3$ | —OCH$_3$ | O | |
| —CH$_2$CH=CH$_2$ | —CH$_3$ | —OCH$_3$ | O | |
| —CH$_2$CH$_2$Cl | —CH$_3$ | —OCH$_3$ | O | |
| —CH$_3$ | —CH$_3$ | —OCH(CH$_3$)COCH$_2$CH$_2$CH$_3$ | O | |
| —CH$_2$CH$_3$ | —CH$_3$ | —CH$_3$ | S | |
| —CH$_2$CH$_2$CH$_3$ | —CH$_3$ | —CH$_3$ | S | |
| —CH(CH$_3$)$_2$ | —CH$_3$ | —CH$_2$OCH$_3$ | O | |
| —CH$_2$CH=CH$_2$ | —CH$_3$ | —CH$_2$CH$_2$OCH$_3$ | O | |
| —CH$_2$CH$_2$Cl | —CH$_3$ | —OCH$_2$CH$_3$ | O | |
| —CH$_3$ | —OCH$_3$ | —OCH$_3$ | O | 99–105° |
| —CH$_2$CH$_3$ | —OCH$_3$ | —CH$_2$OCH$_3$ | O | |
| —CH$_2$CH$_2$CH$_3$ | —OCH$_3$ | —OCH$_2$COCH$_3$ | O | |
| —CH(CH$_3$)$_2$ | —OCH$_3$ | —OCH$_2$COCH$_2$CH$_2$CH$_3$ | O | |
| —CH$_2$CH=CH$_2$ | —OCH$_3$ | —OCH(CH$_3$)COCH(CH$_3$)$_2$ | O | |
| —CH$_2$CH$_2$Cl | —OCH$_3$ | —OCH(CH$_3$)COCH$_3$ | O | |
| —CH$_3$ | —OCH$_3$ | —OCH$_2$CH$_3$ | O | |
| —CH$_3$ | —OCH$_3$ | —OCH$_2$COCH$_2$CH$_3$ | O | |
| —CH$_3$ | —OCH$_3$ | —CH$_2$OCH$_3$ | O | |

TABLE II-continued

Structure: benzene ring with CO₂R (top), CO₂R (bottom), and SO₂NHC(=W)NH- connected to a 6-membered ring with N, N (positions with X and Y via CH₂ groups)

| R | X | Y | W | m.p. |
|---|---|---|---|------|
| —CH₂CH₂Cl | —OCH₃ | —O—CH₂COCH₃ | O | |
| —CH₃ | —OCH₃ | —CH₂CH₂OCH₃ | O | |
| —CH₂CH₃ | —CH₃ | —OCH₂CH₃ | S | |
| —CH₂CH₂CH₃ | —CH₃ | —OCHCOCH₃ (with CH₃) | O | |
| —CH(CH₃)₂ | —CH₃ | —CH₂OCH₃ | O | |
| —CH₂CH=CH₂ | —CH₃ | OCH₂COCH(CH₃)₂ | O | |
| —CH₂CH₂Cl | —CH₃ | —OCH₂CH₃ | O | |
| —CH₃ | —CH₃ | —CH₂CH₂OCH₃ | O | |
| —CH₃ | —CH₃ | —OCHCO₂CH₂CH₃ (with CH₃) | O | 70–80° |
| —CH₃ | —OCH₃ | —OCH₂COCH₃ | O | |
| —CH₃ | —OCH₃ | —OCH₃ | O | 185–186° |
| —CH₂CH₂CH₃ | —CH₃ | —OCH₃ | O | glass |

TABLE III

Structure: benzene ring with CO₂R (top), CO₂R (bottom), SO₂NCO

| R | IR |
|---|---|
| —CH₃ | |
| —CH₂CH₃ | |
| —CH₂CH₂CH₃ | |
| —CH₂CH=CH₂ | |
| —CH₂CH₂Cl | |
| —CH(CH₃)₂ | |

Using the procedures described in Equations 3 and 4, the following compounds may be prepared.

TABLE IV

Structure: benzene ring with CO₂R (top), SO₂NHC(=W)NH- to pyrimidine ring with X and Y, CO₂R (bottom)

| R | X | Y | W | m.p. |
|---|---|---|---|------|
| —CH₃ | —CH₃ | —OCH₃ | O | |
| —CH₂CH₃ | —CH₃ | —OCH₃ | O | |
| —CH₂CH₂CH₃ | —CH₃ | —OCH₃ | O | |
| —CH(CH₃)₂ | —CH₃ | —OCH₃ | O | |
| —CH₂CH=CH₂ | —CH₃ | —OCH₃ | O | |
| —CH₂CH₂Cl | —CH₃ | —OCH₃ | O | |
| —CH₃ | —CH₃ | —OCHCOCH₂CH₂CH₃ (with CH₃) | O | |

TABLE IV-continued

| R | X | Y | W | m.p. |
|---|---|---|---|------|
| —CH₂CH₃ | —CH₃ | —CH₃ | S | |
| —CH₂CH₂CH₃ | —CH₃ | —CH₃ | S | |
| —CH(CH₃)₂ | —CH₃ | —CH₂OCH₃ | O | |
| —CH₂CH=CH₂ | —CH₃ | —CH₂CH₂OCH₃ | O | |
| —CH₂CH₂Cl | —CH₃ | —OCH₂CH₃ | O | |
| —CH₃ | —OCH₃ | —OCH₃ | O | |
| —CH₂CH₃ | —OCH₃ | —CH₂OCH₃ | O | |
| —CH₂CH₂CH₃ | —OCH₃ | —OCH₂COCH₃ | O | |
| —CH(CH₃)₂ | —OCH₃ | —OCH₂COCH₂CH₂CH₃ | O | |
| —CH₂CH=CH₂ | —OCH₃ | —OCHCOCH(CH₃)₂ (with CH₃) | O | |
| —CH₂CH₂Cl | —OCH₃ | —OCHCOCH₃ (with CH₃) | O | |
| —CH₃ | —OCH₃ | —OCH₂CH₃ | O | |
| —CH₃ | —OCH₃ | —OCH₂COCH₂CH₃ | O | |
| —CH₃ | —OCH₃ | —CH₂OCH₃ | S | |

TABLE V

Structure: benzene ring with CO₂R (top), SO₂NHC(=W)NH- to pyrimidine ring with X, Y, CO₂R (bottom)

| R | X | Y | W | m.p. |
|---|---|---|---|------|
| —CH₃ | —OCH₃ | —OCH₂CH₃ | O | |
| —CH₂CH₃ | —OCH₃ | —OCH₃ | O | |
| —CH₂CH₂CH₃ | —OCH₃ | —OCH₃ | O | |
| —CH(CH₃)₂ | —OCH₃ | —OCH₃ | O | |
| —CH₂CH=CH₂ | —OCH₃ | —OCH₂CH₃ | O | |
| —CH₂CH₂Cl | —OCH₃ | —OCH₃ | O | |
| —CH₃ | —OCH₃ | —CH₃ | O | |
| —CH₂CH₃ | —OCH₃ | —OCHCOCH₂CH₂CH₃ (with CH₃) | O | |
| —CH₂CH₂CH₃ | —OCH₃ | —CH₂OCH₃ | S | |
| —CH(CH₃)₂ | —OCH₃ | —CH₂CH₂OCH₃ | S | |
| —CH₂CH=CH₂ | —OCH₃ | —CH₃ | O | |
| —CH₂CH₂Cl | —OCH₃ | —O—CH₂COCH₃ | O | |
| —CH₃ | —OCH₃ | —CH₂CH₂OCH₃ | O | |
| —CH₂CH₃ | —CH₃ | —OCH₂CH₃ | S | |
| —CH₂CH₂CH₃ | —CH₃ | —OCHCOCH₃ (with CH₃) | O | |
| —CH(CH₃)₂ | —CH₃ | —CH₂OCH₃ | O | |
| —CH₂CH=CH₂ | —CH₃ | OCH₂—COCH(CH₃)₂ | O | |
| —CH₂CH₂Cl | —CH₃ | —OCH₂CH₃ | O | |
| —CH₃ | —CH₃ | —CH₂CH₂OCH₃ | O | |

TABLE V-continued

Structure: benzene ring with CO₂R (top), CO₂R (bottom), and SO₂NHC(W)NH— linked to a pyrimidine ring with X and Y substituents.

| R | X | Y | W | m.p. |
|---|---|---|---|---|
| —CH₃ | —CH₃ | —CH₃ | O | |
| —CH₃ | —CH₃ | —OCHCO₂CH₂CH₃ (with CH₃ branch) | O | |
| —CH₃ | —OCH₃ | —OCH₂COCH₃ (C=O) | O | |
| —CH₃ | —OCH₃ | —OCH₃ | O | |
| —CH₂CH₂CH₃ | —CH₃ | —OCH₃ | O | |

TABLE VI

Structure: benzene ring with —C(=O)NRR₁ (top and bottom) and SO₂NHC(W)NH— linked to a pyrimidine with X and Y substituents.

| R | R₁ | X | Y | W | m.p. |
|---|---|---|---|---|---|
| —CH₃ | —CH₃ | —CH₃ | —OCH₃ | O | |
| —CH₂CH₃ | —CH₂CH₃ | —CH₃ | —OCH₃ | O | |
| —CH₂CH₂CH₃ | —CH₂CH₂CH₃ | —CH₃ | —OCH₃ | O | |
| —CH(CH₃)₂ | —CH(CH₃)₂ | —CH₃ | —OCH₃ | O | |
| —CH₂CH=CH₂ | —CH₂CH₃ | —CH₃ | —OCH₃ | O | |
| —CH₃ | —CH₃ | —CH₃ | —OCH(CH₃)COCH₂CH₂CH₃ (C=O) | O | |
| —CH₂CH₃ | —CH₃ | —CH₃ | —CH₃ | S | |
| —CH₂CH₂CH₃ | —CH₂CH₃ | —CH₃ | —CH₃ | S | |
| —CH(CH₃)₂ | —CH₂CH₃ | —CH₃ | —CH₂OCH₃ | O | |
| —CH₂CH=CH₂ | —CH₃ | —CH₃ | —CH₂CH₂OCH₃ | O | |
| —CH₃ | —CH₃ | —OCH₃ | —OCH₃ | S | |
| —CH₂CH₃ | H | —OCH₃ | —CH₂OCH₃ | O | |
| —CH₂CH₂CH₃ | —CH₂CH₃ | —OCH₃ | —OCH₂COCH₃ (C=O) | O | |
| —CH(CH₃)₂ | —CH₃ | —OCH₃ | —OCH₂COCH₂CH₂CH₃ (C=O) | O | |
| —CH₂CH=CH₂ | —CH₃ | —OCH₃ | —OCH(CH₃)COCH(CH₃)₂ (C=O) | O | |
| —CH₃ | —H | —CH₃ | —OCH₃ | O | |
| —CH₃ | H | —OCH₃ | —OCH₂CH₃ | O | |
| —CH₃ | CH₃ | —OCH₃ | —OCH₂COCH₂CH₃ (C=O) | O | |
| —CH₃ | CH₂CH₃ | —OCH₃ | —CH₂OCH₃ | O | |
| cyclopropyl | —CH₃ | —OCH₃ | | O | |
| cyclobutyl | —CH₃ | —OCH₃ | | O | |
| (oxetanyl/CH₂OCH₂) | —CH₃ | —OCH₃ | | O | |
| cyclopropyl | —CH₃ | —OCH(CH₃)—C(=O)—OCH₂CH₂CH₃ | | O | |
| cyclopropyl | —CH₃ | —CH₃ | | S | |
| (oxetanyl/CH₂OCH₂) | —CH₃ | —CH₃ | | O | |
| cyclopropyl | —OCH₃ | —OCH₃ | | O | |

TABLE VI-continued

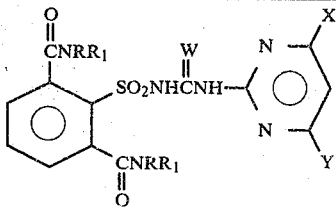

| R | R₁ | X | Y | W | m.p. |
|---|---|---|---|---|---|
| (propyl) | —OCH₃ | —CH₂OCH₃ | | O | |
| (ethoxyethyl) | —OCH₃ | —OCH₂C(O)—OCH₃ | | O | |
| (propyl) | —OCH₃ | —OCH₂C(O)—OCH₂CH₂CH₃ | | O | |
| (propyl) | —OCH₃ | —O—C(CH₃)—C(O)—OCH(CH₃)₂ | | O | |

Also included in Tables I, IV and VI are compounds in which Z=C—CH₃ such as:

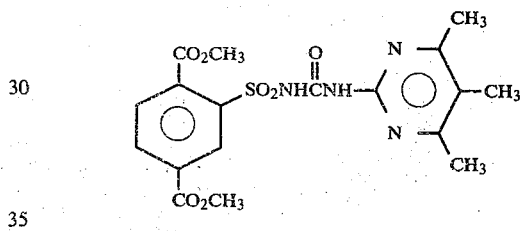

These compounds may also be prepared by procedures taught herein.

TABLE VII

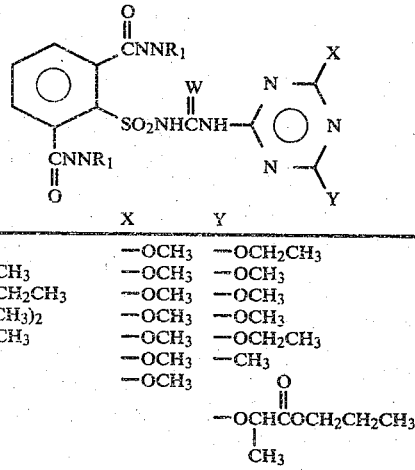

| R | R₁ | X | Y | W | m.p. |
|---|---|---|---|---|---|
| —CH₃ | —CH₃ | —OCH₃ | —OCH₂CH₃ | O | |
| —CH₂CH₃ | —CH₂CH₃ | —OCH₃ | —OCH₃ | O | |
| —CH₂CH₂CH₃ | —CH₂CH₂CH₃ | —OCH₃ | —OCH₃ | O | |
| —CH(CH₃)₂ | —CH(CH₃)₂ | —OCH₃ | —OCH₃ | O | |
| —CH₂CH=CH₂ | —CH₂CH₃ | —OCH₃ | —OCH₂CH₃ | O | |
| —CH₃ | —CH₃ | —OCH₃ | —CH₃ | S | |
| —CH₂CH₃ | —CH₃ | —OCH₃ | —OCHCOCH₂CH₂CH₃ \| CH₃ | O | |
| —CH₂CH₂CH₃ | —CH₂CH₃ | —OCH₃ | —CH₂OCH₃ | O | |
| —CH(CH₃)₂ | —CH₂CH₃ | —OCH₃ | —CH₂CH₂OCH₃ | O | |
| —CH₂CH=CH₂ | —CH₃ | —OCH₃ | —CH₃ | O | |
| —CH₃ | —CH₃ | —OCH₃ | —CH₂CH₂OCH₃ | O | |
| —CH₂CH₃ | —H | —CH₃ | —OCH₂CH₃ | O | |
| —CH₂CH₂CH₃ | —CH₂CH₃ | —CH₃ | —OCHCOCH₃ \| CH₃ | O | |
| —CH(CH₃)₂ | —CH₃ | —CH₃ | —CH₂OCH₃ | O | |
| —CH₂CH=CH₂ | —CH₃ | —CH₃ | OCH₂COCH(CH₃)₂ | O | |

TABLE VII-continued

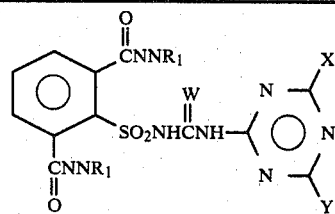

| R | R₁ | X | Y | W | m.p. |
|---|----|---|---|---|------|
| —CH$_3$ | —H | —CH$_3$ | —CH$_2$CH$_2$OCH$_3$ | O | |
| —CH$_3$ | —CH$_3$ | —CH$_3$ | —OCH(CH$_3$)CO$_2$CH$_2$CH$_3$ | O | |
| —CH$_3$ | —CH$_2$CH$_3$ | —OCH$_3$ | —OCH$_2$COCH$_3$ | O | |
| —CH$_3$ | —CH$_3$ | —OCH$_3$ | —OCH$_3$ | O | |
| —CH$_2$CH$_2$CH$_3$ | —CH$_3$ | —OCH$_3$ | —OCH$_3$ | O | |
| ⟩ | | —CH$_3$ | —OCH$_3$ | O | |
| ⟩ | | —CH$_3$ | —OCH$_3$ | O | |
| ⟩O | | —CH$_3$ | —OCH$_3$ | O | |
| ⟩ | | —CH$_3$ | —OCH(CH$_3$)—C(O)—OCH$_2$CH$_2$CH$_3$ | O | |
| ⟩ | | —CH$_3$ | —CH$_3$ | S | |
| ⟩O | | —CH$_3$ | —CH$_3$ | O | |
| ⟩ | | —OCH$_3$ | —OCH$_3$ | O | |
| ⟩ | | —OCH$_3$ | —CH$_2$OCH$_3$ | O | |
| ⟩O | | —OCH$_3$ | —OCH$_2$C(O)—OCH$_3$ | O | |
| ⟩ | | —OCH$_3$ | —OCH$_2$C(O)—OCH$_2$CH$_2$CH$_3$ | O | |
| ⟩ | | —OCH$_3$ | —O—C(CH$_3$)—C(O)—OCH(CH$_3$)$_2$ | O | |

FORMULATIONS

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table 3.

TABLE VIII

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., N.Y., 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, N.Y., 1973, pp. 8–57 ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182.

H. Gysin and E. Knusli, U.S. Pat. No. 2,891,855, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

Unless indicated otherwise, all parts are by weight in the following examples.

EXAMPLE 12

Wettable Powder

| | |
|---|---|
| 2-{[(4,6-Dimethyl-1,3,5-triazin-2-yl)aminocarbonyl]-aminosulfonyl}-1,4-benzenedicarboxylic acid, dimethyl ester | 90% |
| dioctyl sodium sulfosuccinate | 0.1% |
| sodium ligninsulfonate | 1% |
| synthetic fine silica | 8.9% |

The ingredients are blended and ground in a hammer-mill to produce particles almost all of which are below 100 microns in size. The product is sifted through a U.S.S. No. 50 screen and packaged.

EXAMPLE 13

Granule

| | |
|---|---|
| wettable powder of Example 12 | 10% |
| attapulgite granules (U.S.S. #20–40; 0.84–0.42 mm) | 90% |

A slurry of wettable powder containing 50% solids is sprayed on the surface of attapulgite granules in a double-cone blender. The granules are dried and packaged.

EXAMPLE 14

Wettable Powder

| | |
|---|---|
| 2-{[(4,6-Dimethylpyrimidin-2-yl)aminocarbonyl]aminosulfonyl}-1,4-benzenedicarboxylic acid, dimethyl ester | 80% |
| sodium alkylnaphthalenesulfonate | 2% |
| sodium ligninsulfonate | 2% |
| synthetic amorphous silica | 3% |
| kaolinite | 13% |

The ingredients are thoroughly blended and ground in a hammer mill to produce particles essentially all of which are under 100 microns in size; the material is reblended, sifted through a U.S.S. No. 50 sieve and packaged.

EXAMPLE 15

Granule

| | |
|---|---|
| wettable powder of Example 14 | 25% |
| gypsum | 64% |
| potassium sulfate | 11% |

The ingredients are blended in a rotating mixer and water is sprayed onto the powder to accomplish granulation. When most of the material has reached the desired range of 1.0 to 0.42 mm. (U.S.S. #18 to 40 mesh), the granules are removed, dried, and screened. Oversize material is crushed to produce additional material in the desired range. These granules contain 20% active ingredient.

EXAMPLE 16

Wettable Powder

| | |
|---|---|
| 2-{[(4,6-Dimethoxy-1,3,5-triazin-2-yl)aminocarbonyl]-aminosulfonyl}-1,4-benzenedicarboxylic acid, dimethyl ester | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended, sifted through a U.S.S. No. 50 sieve (0.3 mm opening) and packaged.

EXAMPLE 17

Wettable Powder

| | |
|---|---:|
| 2-{[(4-Methoxy-5-methylpyrimidin-2-yl)aminocarbonyl]-aminosulfonyl}-1,4-benzenedicarboxylic acid, dimethyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air milled to produce particles essentially all below 10 microns in diameter. The product is reblended before packaging.

EXAMPLE 18

Oil Suspension

| | |
|---|---:|
| 2-{([4-(2-Ethoxy-1-methyl-2-oxoethoxy)-6-methyl-1,3,5-triazin-2-yl]aminocarbonyl)aminosulfonyl}-1,4-benzenedicarboxylic acid, dimethyl ester | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspensions may be applied directly, but preferably after being extended with oils or emulsified in water.

EXAMPLE 19

Aqueous Suspension

| | |
|---|---:|
| 2-{[(4,6-Dimethoxypyrimidin-2-yl)aminocarbonyl]aminosulfonyl}-1,4-benzenedicarboxylic acid, dimethyl ester | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 20

Extruded Pellet

| | |
|---|---:|
| 2-{[(4-Methoxy-6-methyl-1,3,5-triazin-2-yl)aminocarbonyl]-aminosulfonyl}-1,4-benzenedicarboxylic acid, dimethyl ester | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 21

Solution

| | |
|---|---:|
| 2-{[(4,6-Dimethoxypyrimidin-2-yl)aminocarbonyl]amino-sulfonyl}-1,4-benzenedicarboxylic acid, dipropyl ester | 5% |
| dimethylformamide | 95% |

The ingredients are combined and stirred to produce a solution, which can be used for low volume applications.

UTILITY

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful for the selective pre- or post-emergence weed control in crops, such as wheat, cotton, soybeans and corn. The compounds are particularly useful for the post-emergence control of weeds in corn.

The rates of application for the compounds of the invention are determined by a number of factors, including their use as selective or general herbicides, the crop species involved, the types of weeds to be controlled, weather and climate, formulations selected, mode of application, amount of foilage present, etc. In general terms, the subject compounds should be applied at levels of around 0.10 to 20 kg/ha, the lower rates being suggested for use on lighter soils and/or those having a low organic matter content, for selective weed control or for situations where only short-term persistence is required.

The compounds of Formula I may be combined with other herbicides and are particularly useful in combination with 3-(3,4-dichlorophenyl)-1,1-dimethyl urea; the triazines such as 2-chloro-4-(ethylamino)-6-(isopropylamino)-s-triazine: the uracils such as 5-bromo-3-sec-butyl-6-methyluracil; N-(phosponomethyl)-glycine; 3-cyclohexyl-1-methyl-6-dimethylamino-s-triazine-2,4(1H,3H)-dione; N,N-dimethyl-2,2-diphenyl-acetamide; 2,4-dichlorophenoxyacetic acid (and closely related compounds); 4-chloro-2-butynyl-3-chlorophenyl-carbamate; diisopropylthiolcarbamic acid, ester with 2,3-dichloroallyl alcohol; diisopropylthiolcarbamic acid, S-(2,3,3-trichloroallyl)ester; ethyl-N-benzoyl-N-(3,4-dichlorophenyl)-2-aminopropionate; 1,2-dimethyl-3,5-diphenylpyrazolium methylsulfate; methyl 2-[4-(2,4-dichlorophenoxy)-phenoxy]propanoate; 4-amino-6-tert-butyl-3-(methylthio)-1,2,4-triazin-5(4H)-one; 3-(3,4-dichlorophenyl)-1-methoxy-1-methylurea; 3-isopropyl-1H-2,1,3-benzothiodiazin-(4)-3H-one-2,2-dioxide; $\alpha,\alpha,\alpha$-trifluoro-2,6-dinitro-N,N-dipropyl-p-toluidine; 1,1'-dimethyl-4,4'-bipyridinium ion; monosodium methaneasonate; 2-chloro-2',6'-diethyl(methoxymethyl)-acetanilide; and 1,1-dimethyl-3-($\alpha,\alpha,\alpha$-trifluoro-m-tolyl)-urea.

The activity of these compounds was discovered in greenhouse tests. The tests are described and the data resulting from them are shown below.

Test Procedure A

Seeds of crabgrass (Digitaria spp.), barnyardgrass (Echinochloa crusgalli), wild oats (Avena fatua), cassia (Cassia tora), morningglory (Ipomoea spp.), cocklebur (Xanthium spp.), sorghum, corn, soybean, rice, wheat and nutsedge tubers (Cyperus rotundus) were planted in a growth medium and treated preemergence with a nonphytotoxic solvent solution of the compounds of Test A. At the same time, cotton having five leaves (including cotyledonary ones), bush beans with the third trifoliate leaf expanding, crabgrass with two leaves, barnyardgrass with two leaves, wild oats with two leaves, cassia with three leaves, (including cotyledonary ones), morningglory with four leaves (including the cotyledonary ones), cocklebur with four leaves (including the cotyledonary ones), sorghum with four leaves, corn with four leaves, soy-bean with two cotyledonary leaves, rice with three leaves, wheat with one leaf, and nutsedge with three-five leaves were sprayed with a nonphytotoxic solvent solution of the compounds of Test A. Other containers of the above mentioned weeds and crops were treated pre- or post-emergence with the same nonphytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment, using the following rating system and symbols.

0 = no effect
10 = maximum effect
C = chlorosis or necrosis
D = defoliation
E = emergence inhibition
G = growth retardation
H = formative effects
U = unusual pigmentation

TEST A

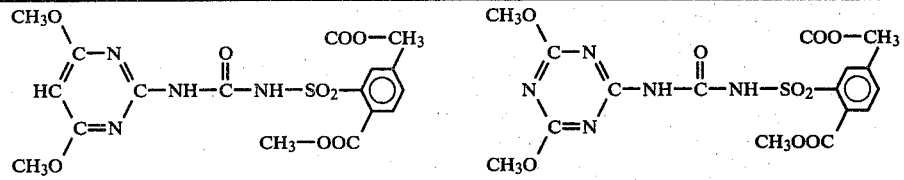

| | | |
|---|---|---|
| Rate, kg/ha | 0.4 | 0.4 |
| POST-EMERGENCE | | |
| BUSHBEAN | 9C | 9C |
| COTTON | 9C | 4C,9G |
| MORNINGGLORY | 10C | 2C,8G |
| COCKLEBUR | 10C | 5G |
| CASSIA | 9C | 2G |
| NUTSEDGE | 7C | 0 |
| CRABGRASS | 1C,7G | 0 |
| BARNYARDGRASS | 2C,7H | 1C |
| WILD OATS | 2C,8G | 2C,5G |
| WHEAT | 10C | 2C,6G |
| CORN | 2C,9H | 1C,5H |
| SOYBEAN | 3C,7G | 2C,5G |
| RICE | 3C,8G | 3C,8G |
| SORGHUM | 2C,8G | 2C,9G |
| PRE-EMERGENCE | | |
| MORNINGGLORY | 9G | 8G |
| COCKLEBUR | 8G | 1C,5H |
| CASSIA | 7G | 1C,5G |
| NUTSEDGE | 9G | 10E |
| CRABGRASS | 2G | 3G |
| BARNYARDGRASS | 1C,6G | 2C |
| WILD OATS | 4G | 2C,6G |
| WHEAT | 9H | 9H |
| CORN | 1C,3G | 2C,8G |
| SOYBEAN | 0 | 0 |
| RICE | 10E | 10E |
| SORGHUM | 1C,9H | 1C |

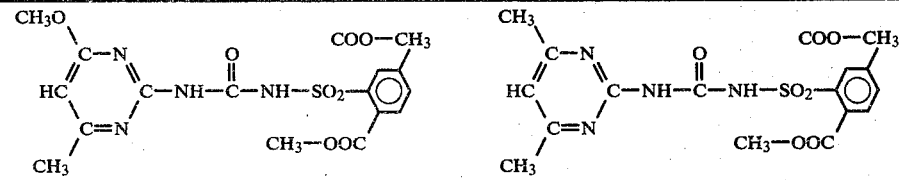

| | | |
|---|---|---|
| Rate, kg/ha | 0.4 | 0.4 |
| POST-EMERGENCE | | |
| BUSHBEAN | 4C,9G,6Y | 9C |
| COTTON | 4C,9G | 5C,9G |
| MORNINGGLORY | 10C | 2C,8G |
| COCKLEBUR | 9C | 2C,6G |
| CASSIA | 5C,9G | 2C,8G |
| NUTSEDGE | 4G | 3G |
| CRABGRASS | 2G | 2G |

TEST A-continued

| | | |
|---|---|---|
| BARNYARDGRASS | 1C,2H | 1C |
| WILD OATS | 1C,6G | 3C,7G |
| WHEAT | 3C,9G | 9C |
| CORN | 2C | 1H |
| SOYBEAN | 7C | 2H |
| RICE | 9C | 2C,8G |
| SORGHUM | 2C,9H | 2C,9G |
| PRE-EMERGENCE | | |
| MORNINGGLORY | 9G | 9G |
| COCKLEBUR | 8G | 8G |
| CASSIA | 7G | 8G |
| NUTSEDGE | 9G | 10E |
| CRABGRASS | 1C,8G | 4G |
| BARNYARDGRASS | 2C,7G | 5C |
| WILD OATS | 2C,8H | 2C,5H |
| WHEAT | 9H | 9H |
| CORN | 1C,2G | 3G |
| SOYBEAN | 1C,4G | 3G |
| RICE | 10E | 10E |
| SORGHUM | 9G | 9G |

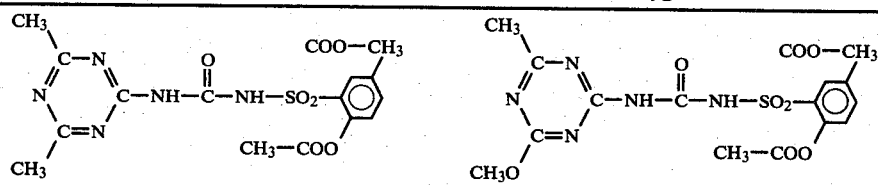

| Rate, kg/ha | 0.4 | 0.4 |
|---|---|---|
| POST-EMERGENCE | | |
| BUSHBEAN | 3C,7D,6Y | 9C |
| COTTON | 1C | 5C,7G |
| MORNINGGLORY | 2C,5G | 9C |
| COCKLEBUR | 2C,7G | 10C |
| CASSIA | 2C | 1C,5G |
| NUTSEDGE | 0 | 1C |
| CRABGRASS | 0 | 3G |
| BARNYARDGRASS | 0 | 0 |
| WILD OATS | 0 | 1C,7G |
| WHEAT | 1C,3G | 2C,8G |
| CORN | 0 | 1C,4G |
| SOYBEAN | 0 | 1H,6G |
| RICE | 0 | 9G |
| SORGHUM | 2C,8G | 9H |
| PRE-EMERGENCE | | |
| MORNINGGLORY | 5G | 9G |
| COCKLEBUR | 6G | 9G |
| CASSIA | 2C,5G | 2C,9G |
| NUTSEDGE | 0 | 3G |
| CRABGRASS | 0 | 0 |
| BARNYARDGRASS | 1H | 0 |
| WILD OATS | 1H | 2C,8H |
| WHEAT | 7G | 9H |
| CORN | 0 | 2C,5G |
| SOYBEAN | 0 | 1H,5G |
| RICE | 9H | 9H |
| SORGHUM | 8G | 9H |

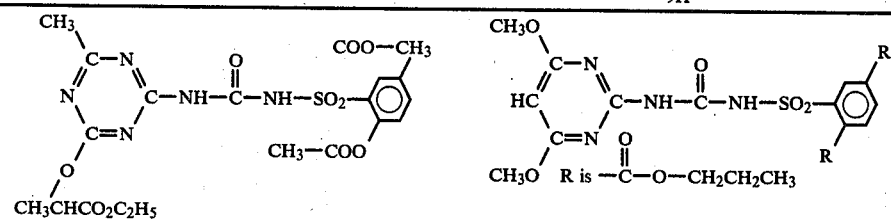

| Rate, kg/ha | 0.4 | 0.4 |
|---|---|---|
| POST-EMERGENCE | | |
| BUSHBEAN | 3C,7G,6Y | 3C,5G,6Y |
| COTTON | 0 | 3B |
| MORNINGGLORY | 1C | 2C,5H |
| COCKLEBUR | 5G | 2C,5G |
| CASSIA | 0 | 1C |
| NUTSEDGE | 0 | 0 |
| CRABGRASS | 0 | 0 |
| BARNYARDGRASS | 0 | 1C |
| WILD OATS | 0 | 0 |

TEST A-continued

| | | |
|---|---|---|
| WHEAT | 0 | 1C |
| CORN | 0 | 1C |
| SOYBEAN | 0 | 1C,2H |
| RICE | 5G | 2G |
| SORGHUM | 7G | 1C |
| PRE-EMERGENCE | | |
| MORNINGGLORY | 7G | 2G |
| COCKLEBUR | 8G | 5G |
| CASSIA | 0 | 1C |
| NUTSEDGE | 0 | 2G |
| CRABGRASS | 0 | 2G |
| BARNYARDGRASS | 1H | 2C,5G |
| WILD OATS | 0 | 2G |
| WHEAT | 7G | 2G |
| CORN | 1C | 1C,3G |
| SOYBEAN | 1C | 0 |
| RICE | 9H | 2C,9H |
| SORGHUM | 6G | 2C,4G |

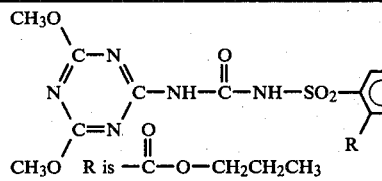 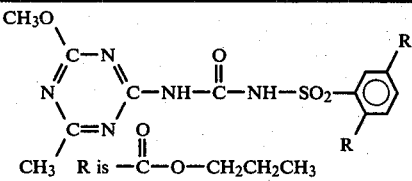

| Rate, kg/ha | 0.4 | 0.4 |
|---|---|---|
| POST-EMERGENCE | | |
| BUSHBEAN | 3S,6G,6Y | 2S,8G,6Y |
| COTTON | 2B,1H | 1B,2C |
| MORNINGGLORY | 1B | 1B |
| COCKLEBUR | 1B | 1B |
| CASSIA | 1B | 1B |
| NUTSEDGE | 0 | 0 |
| CRABGRASS | 0 | 0 |
| BARNYARDGRASS | 0 | 0 |
| WILD OATS | 0 | 0 |
| WHEAT | 0 | 0 |
| CORN | 2G | 2G |
| SOYBEAN | 0 | 1C |
| RICE | 0 | 0 |
| SORGHUM | 0 | 0 |
| PRE-EMERGENCE | | |
| MORNINGGLORY | 2G | 2G |
| COCKLEBUR | 3G | 5G |
| CASSIA | 0 | 0 |
| NUTSEDGE | 0 | 0 |
| CRABGRASS | 0 | 0 |
| BARNYARDGRASS | 1C | 1C |
| WILD OATS | 0 | 0 |
| WHEAT | 0 | 0 |
| CORN | 0 | 0 |
| SOYBEAN | 0 | 0 |
| RICE | 0 | 0 |
| SORGHUM | 0 | 0 |

Test B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avenua fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of this invention.

Twenty-eight days after treatment, the plants were evaluated and visually rated for response to the chemical treatments utilizing the rating system described previously for Test A. The data are summarized in Test B. Note that certain compounds are useful as pre-emergence treatments for weed control in crops such as soybeans, corn, wheat and cotton.

Test B

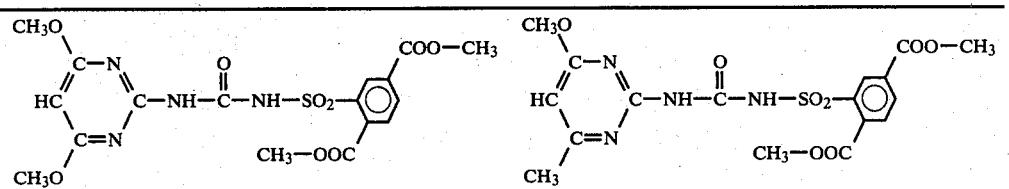

| Rate, kg/ha | 0.125 | 0.5 | 0.125 | 0.5 |
|---|---|---|---|---|
| Crabgrass | 0 | 0 | 0 | 0 |
| Barnyardgrass | 0 | 5G | 3G | 3G |
| Sorghum | 3G | 3G | 3G | 5G |
| Wild Oats | 0 | 4G | 0 | 3G |
| Johnsongrass | 0 | 3G | 0 | 2G |
| Dallisgrass | 0 | 0 | 0 | 3G |
| Giant foxtail | 0 | 3H | 0 | 0 |
| Ky. bluegrass | 5G | 7G,5C | 0 | 6G |
| Cheatgrass | 3G | 7G,5E | 5G | 7G,5E |
| Sugarbeets | 0 | 4G,5E | 2G | 6G,8E |
| Corn | 0 | 2G | 0 | 0 |
| Mustard | 7G | 8G,5C | 6G | 8G |
| Cocklebur | — | 6G | 0 | 2G |
| Pigweed | 7G,5C | 8G,8C | 7G,5C | 8G,8C |
| Nutsedge | 0 | 6G,3C | 0 | 0 |
| Cotton | 0 | 3G | 0 | 0 |
| Morningglory | 0 | 8G | 0 | 6G |
| Cassia | 0 | 2G | 0 | 0 |
| Teaweed | 0 | 0 | 0 | 0 |
| Velvetleaf | 0 | 0 | 0 | 5G |
| Jimsonweed | 0 | 0 | 0 | 0 |
| Soybean | 0 | 0 | 0 | 0 |
| Rice | 5G,3C | 8G,8C | 3G | 7G,4C |
| Wheat | 0 | 0 | 0 | 0 |

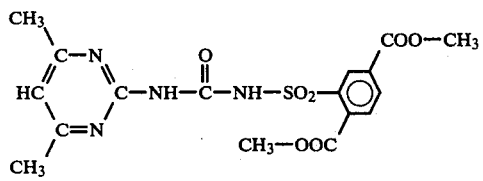

| Rate, kg/ha | 0.125 | 0.5 |
|---|---|---|
| Crabgrass | 0 | 0 |
| Barnyardgrass | 0 | 0 |
| Sorghum | 0 | 0 |
| Wild Oats | 0 | 0 |
| Johnsongrass | 0 | 2G |
| Dallisgrass | 0 | 3G |
| Giant foxtail | 0 | 0 |
| Ky. bluegrass | 0 | 0 |
| Cheatgrass | 0 | 2G |
| Sugarbeets | 0 | 0 |
| Corn | 0 | 0 |
| Mustard | 2G | 3G |
| Cocklebur | 0 | 0 |
| Pigweed | 0 | 3G |
| Nutsedge | 0 | 0 |
| Cotton | 0 | 3H |
| Morningglory | 0 | 0 |
| Cassia | 0 | 0 |
| Teaweed | 0 | 0 |
| Velvetleaf | 0 | 0 |
| Jimsonweed | 0 | 0 |
| Soybean | 0 | 0 |
| Rice | 0 | 3G,3C |
| Wheat | 0 | 0 |

Test C

Twenty-five cm diameter plastic pots filled with Fallsington silt loam were planted to soybeans, cotton, alfalfa, corn, rice, wheat, sorghum, velvetleaf, (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Sestaria faberii*) and wild oats (*Avenua fatua*). Approximately 2-½ weeks after planting, the young plants and the soil around them were sprayed overall with the test chemical dissolved in a nonphytotoxic solvent. Fourteen days after treatment, all species were compared to untreated controls and visually rated for response to treatment. The rating system was as described previously for Test A. The data are presented in Test C.

kochia (*Kochia scoparia*), shepherd's purse (*Capsella bursapastoris*), false chamomile (*Matricaria inodora*), black nightshade (*Solanum nigrum*), yellow rocket Test C

| | | | | |
|---|---|---|---|---|
| Rate, kg/ha | 0.125 | 0.5 | 0.125 | 0.5 |
| Velvetleaf | — | — | — | — |
| Sesbania | — | — | — | — |
| Cassia | — | — | — | — |
| Cotton | 10G,9C | 10C | 10C | 10C |
| Morningglory | 10C | 10C | 10C | 10C |
| Alfalfa | 5G | 8G,3C | 8G,7C | 2G |
| Jimsonweed | 10G,9C | 10G,9C | 5G | 10G,9C |
| Cocklebur | 10C | 10C | — | 10C |
| Corn | 0 | 2C | 0 | 0 |
| Crabgrass | 0 | 5G | 0 | 0 |
| Rice | — | — | — | — |
| Nutsedge | — | 3G | 0 | 2G |
| Barnyardgrass | 0 | 0 | 0 | 2G |
| Wheat | 3G | 7G | 7G | 8G |
| Giant Foxtail | 10G,5H | 10C | 10G,8C | 10G,3H |
| Wild Oats | 8G | 8G,3C | 8G | 9G,2C |
| Sorghum | 8G,3C | 10G,3C | 10G,3C | 10G,3C |
| Soybean | 10G,9C | 10C | 10C | 10G,8C |

Test D

Two ten-inch in diameter plastic pans lined with polyethylene liners were filled with prepared Fallsington silt loam soil. One pan was planted with seeds of wheat (*Triticum aestivum*), barley (*Hordeum vulgare*), wild oats (*Avena fatua*), downy brome (*Bromus tectorum*), cheatgrass (*Bromus secalinus*), blackgrass (*Alopecurus myosuroides*), annual bluegrass (*Poa annua*), green foxtail (*Setaria viridis*), quackgrass (*Agropyron repens*), Italian ryegrass (*Lolium multiflorum*) and ripgut brome (*Bromus rigidus*). The other pan was planted with seeds of Russian thistle (*Salsola Kali*), tansy mustard (*Descurainia pinnata*), smartweed (*Polygonum pennsylvanicum*), jimhill mustard (*Sisymbrium altissimum*), (*Barbarea vulgaris*), wild mustard (*Brassica kaber*) and wild buckwheat (*Polygonum convolvulus*). The above two pans were treated pre-emergence. At the same time, two pans in which the above plant species were growing were treated post-emergence. Plant height at the time of treatment ranged from 1-15 cm depending on plant species.

The compounds applied were diluted with a non-phytotoxic solvent and sprayed over-the-top of the pans. An untreated control and a solvent-alone control were included for comparison. All treatments were maintained in the greenhouse for 20 days at which time the treatments were compared to the controls and the effects visually rated. The recorded date are presented in Test D.

Test D

| Rate, kg/ha | 0.06 | 0.25 |
|---|---|---|
| Pre-emergence | | |
| wheat | 0 | 0 |
| barley | 0 | 0 |
| wild oats | 0 | 0 |
| downy brome | 1G | 5G |
| cheatgrass | 1G | 5G |
| blackgrass | 2G | 1C,3G |
| annual bluegrass | 1G | 3G |
| green foxtail | 0 | 2C,2G |
| quackgrass | 1G | 1C,3G |
| Italian ryegrass | 2G | 2G |
| ripgut brome | 0 | 0 |
| Russian thistle | 1G | 1G |
| tansy mustard | 8G | 7C,9G |
| smartweed | 3G | 5C,5G |
| jimhill mustard | 7G | 3C,8G |
| kochia | 5G | 5G |
| shepherd's purse | 8G | 7C,8G |

Test D-continued

| | | |
|---|---|---|
| false chamomile | 1C,6G | 4C,8G |
| black nightshade | 1C,2G | 3C,3G |
| yellow rocket | 7G | 2C,7G |
| wild mustard | 7G | 4C,8G |
| wild buckwheat | 2G | 3C,3G |
| Post-emergence | | |
| wheat | 1C,2G | 7C |
| barley | 3C,7G | 8C |
| wild oats | 0 | 5C,4G |
| downy brome | 1C,4G | 4C,7G |
| cheatgrass | 6C,5G | 8C |
| blackgrass | 4C,5G | 7C |
| annual bluegrass | 2C,3G | 5C,5G |
| green foxtail | 4C,5G | 7C |
| quackgrass | 3C,4G | 5C,5G |
| Italian ryegrass | 2C,2G | 5C,7G |
| ripgut brome | 1C,4G | 7C |
| Russian thistle | 5C | 8C |
| tansy mustard | 3C,5G | 5C,5G |
| smartweed | 5C,5G | 7C |
| jimhill mustard | 9C | 9C |
| kochia | 2G | 5C,7G |
| shepherd's purse | 7C | 9C |
| false chamomile | 8C,8G | 9C,9G |
| black nightshade | 4C,4G | 7C,7G |
| yellow rocket | 8C | 9C |
| wild mustard | 10C | 10C |
| wild buckwheat | 1C,3G | 4C,3G |

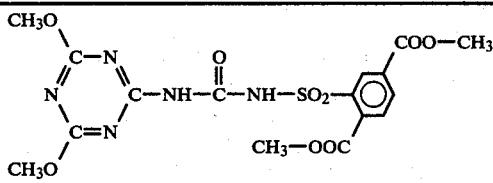

| Rate, kg/ha | 0.06 | 0.25 |
|---|---|---|
| Pre-emergence | | |
| wheat | 0 | 0 |
| barley | 0 | 0 |
| wild oats | 0 | 0 |
| downy brome | 0 | 0 |
| cheatgrass | 0 | 0 |
| blackgrass | 0 | 0 |
| annual bluegrass | 0 | 0 |
| green foxtail | 0 | 0 |
| quackgrass | 0 | 0 |
| Italian ryegrass | 0 | 0 |
| ripgut brome | 0 | 0 |
| Russian thistle | 0 | 0 |
| tansy mustard | 0 | 3G |
| smartweed | 0 | 2G |
| jimhill mustard | 0 | 2G |
| kochia | 0 | 0 |
| shepherd's purse | 0 | 2G |
| false chamomile | 0 | 0 |
| black nightshade | 0 | 0 |
| yellow rocket | 0 | 0 |
| wild mustard | 0 | 0 |
| wild buckwheat | 0 | 0 |
| Post-emergence | | |
| wheat | 3C,3G | 7C |
| barley | 9C | 9C |
| wild oats | 0 | 3C |
| downy brome | 4G | 2C,5G |
| cheatgrass | 6C,5G | 7C |
| blackgrass | 7C | 7C |
| annual bluegrass | 1C,2G | 4C,5G |
| green foxtail | 6C | 7C |
| quackgrass | 4C,4G | 5C,5G |
| Italian ryegrass | 7C | 8C |
| ripgut brome | 10C | 9C |
| Russian thistle | 2C | 5C |
| tansy mustard | 0 | 3C,4G |
| smartweed | 2G | 6C |
| jimhill mustard | 5C,5G | 10C |
| kochia | 0 | 0 |
| shepherd's purse | 2G | 8C |
| false chamomile | 0 | 2C,3G |
| black nightshade | 1C,2G | 8C |
| yellow rocket | 5C,5G | 8C |

Test D-continued

| | | |
|---|---|---|
| wild mustard | 7C | 8C |
| wild buckwheat | 0 | 2C,3G |

What is claimed is:

1. A compound selected from

<chemical structure> wherein
Q is O or
$$-\underset{R_1}{N}-;$$

W is O or S;
when Q is O, then R is $C_1$-$C_4$ alkyl, $C_3$-$C_4$ alkenyl, $CH_2CH_2Cl$ or $CH_2CH_2OCH_3$;
when Q is
$$-\underset{R_1}{N}-,$$

then R is H, $C_1$-$C_4$ alkyl or $C_3$-$C_4$ alkenyl;
$R_1$ is H, $C_1$-$C_4$ alkyl, and R and $R_1$ can be taken together to form $-(CH_2)_4-$, $-(CH_2)_5-$, and $-CH_2CH_2O-CH_2CH_2-$;
X is $CH_3$, $CH_3O$, $CH_2CH_3O$ or Cl;
Y is $CH_3$, $CH_3O(CH_2)_{n'}$, where n' is 0, 1 or 2, $CH_3CH_2O$, or $R^2O_2CCHR^1O$ where $R^1$ is H or $CH_3$ and $R^2$ is H or $C_1$-$C_3$ alkyl;
Z is CH, or C—$CH_3$;
with the proviso that when Q is
$$-\underset{R_1}{N}-,$$

then the floating $$-\underset{R_1}{\overset{O}{\underset{\|}{C}}-N-R}$$

must be in the 3 position.

2. Compounds of claim 1 wherein W is O.
3. Compounds of claim 2 wherein Q is oxygen.
4. Compounds of claim 3 wherein Y is $CH_3-$, $-OCH_3$ or $$-OCHCO_2H,$$
$$\underset{CH_3}{|}$$

and X is $CH_3$, $CH_3O$ or $CH_3CH_2O$.

5. Compounds of claim 4 wherein R is $CH_3$ or $-CH_2CH_3$.

6. The compound of claim 1,
2-{[(4,6-Dimethoxypyrimidin-2-yl)aminocarbonyl]aminosulfonyl}-1,4-benzenedicarboxylic acid, dimethyl ester.

7. The compound of claim 1,
2-{[(4-Methoxy-6-methylpyrimidin-2-yl)aminocarbonyl]-aminosulfonyl}-1,4-benzenedicarboxylic acid, dimethyl ester.

8. The compound of claim 1,
2-{[(4,6-Dimethylpyrimidin-2-yl)aminocarbonyl]aminosulfonyl}-1,4-benzenedicarboxylic acid, dimethyl ester.

9. The compound of claim 1,
2-{[(4,6-Dimethoxypyrimidin-2-yl)aminocarbonyl]aminosulfonyl}-1,4-benzenedicarboxylic acid, dipropyl ester.

10. A composition for the control of undesirable vegetation consisting essentially of an effective amount of a compound of claim 1 and at least one of (a) a surface-active agent and (b) a solid or liquid diluent.

11. A composition for the control of undesirable vegetation consisting essentially of an effective amount of a compound of claim 2 and at least one of (a) a surface-active agent and (b) a solid or liquid diluent.

12. A composition for the control of undesirable vegetation consisting essentially of an effective amount of a compound of claim 3 and at least one of (a) a surface-active agent and (b) a solid or liquid diluent.

13. A composition for the control of undesirable vegetation consisting essentially of an effective amount of a compound of claim 4 and at least one of (a) a surface-active agent and (b) a solid or liquid diluent.

14. A composition for the control of undesirable vegetation consisting essentially of an effective amount of the compound of claim 5 and at least one of (a) a surface-active agent and (b) a solid or liquid diluent.

15. A method for the control of undesirable vegetation comprising applying to the locus of such undesirable vegetation a herbicidally effective amount of a compound of claim 1.

16. A method for the control of undesirable vegetation comprising applying to the locus of such undesirable vegetation a herbicidally effective amount of a compound of claim 2.

17. A method for the control of undesirable vegeation comprising applying to the locus of such undesirable vegetation a herbicidally effective amount of a compound of claim 3.

18. A method for the control of undesirable vegetation comprising applying to the locus of such undesirable vegetation a herbicidally effective amount of a compound of claim 4.

19. A method for the control of undesirable vegetation comprising applying to the locus of such undesirable vegetation a herbicidally effective amount of the compound of claim 5.

* * * * *